United States Patent [19]

Bracco et al.

[11] 4,352,746

[45] Oct. 5, 1982

[54] PROCESS FOR THE PRODUCTION OF OXIDATION-INHIBITING SUBSTANCES

[75] Inventors: Umberto Bracco; Jean-Louis Viret, both of La Tour-de-Peilz; Josef Rehacek, Yverdon, all of Switzerland

[73] Assignee: Societe d'Assistance Technique Pour Produits Nestle S.A., Lausanne, Switzerland

[21] Appl. No.: 283,526

[22] Filed: Jul. 15, 1981

Related U.S. Application Data

[63] Continuation of Ser. No. 77,847, Sep. 21, 1979, abandoned.

[30] Foreign Application Priority Data

Sep. 29, 1978 [CH] Switzerland ............... 10186/78

[51] Int. Cl.$^3$ ................. A23B 4/00; A23B 5/00; A23B 9/00; C09K 15/34
[52] U.S. Cl. ................. 252/398; 426/542; 426/654; 426/655; 426/429
[58] Field of Search .......... 426/542, 655, 429, 330, 426/654; 252/398

[56] References Cited

U.S. PATENT DOCUMENTS

| | | | |
|---|---|---|---|
| 2,176,030 | 10/1939 | Musher | 426/542 |
| 2,221,404 | 11/1940 | Musher | 426/542 |
| 2,752,314 | 6/1956 | Clopton | 426/542 X |
| 2,950,975 | 8/1960 | Hervey | 426/542 |
| 3,497,362 | 2/1970 | Patron et al. | 426/542 |
| 3,732,111 | 5/1973 | Berner et al. | 426/542 |
| 3,950,266 | 4/1976 | Chang et al. | 426/542 X |

OTHER PUBLICATIONS

Chemical Abstracts, vol. 60, 1964, 2251g.
Bracco, U. "Medium-Chain Triglycerides: Characteristics and Uses," in: Lipids, vol. 2: Technology, Raven Press, New York, 1976, pp. 401-409.

*Primary Examiner*—Robert A. Yoncoskie
*Attorney, Agent, or Firm*—Vogt & O'Donnell

[57] ABSTRACT

The invention relates to a process for the production of a fraction containing oxidation-inhibiting substances from a vegetable material rich in these substances, to the fraction thus obtained and to its use for stabilizing food and cosmetic products against oxidation. The process is characterized in that the previously ground vegetable material or an extract of this vegetable material obtained with a light solvent, a distillation vehicle and an oil are mixed, the suspension is subjected to molecular distillation and a condensate containing the oxidation-inhibiting principles, the distillation vehicle and some of the oil used is collected.

8 Claims, No Drawings

PROCESS FOR THE PRODUCTION OF OXIDATION-INHIBITING SUBSTANCES

This is a continuation of application Ser. No. 077,847, filed Sept. 21, 1979, now abandoned.

This invention relates to a process for the production of a fraction containing oxidation-inhibiting substances from a vegetable material rich in these substances, to the fraction thus obtained and to its use for stabilising food and cosmetic products against oxidation.

Oxidation inhibitors of the type generally used in foods and cosmetics are required to show high oxidation-inhibiting activity and to be stable, colourless, organoleptically neutral and harmless.

Synthetically obtained oxidation-inhibiting substances are known and are very widely used in the food industry. They are generally phenolic substances, for example butyl hydroxy anisole (B.H.A) and butyl hydroxy toluene (B.H.T.), which are used either on their own or in the form of synergic mixtures. Although these substances show pronounced oxidation-inhibiting activity and high stability and although they are colourless and both harmless and neutral with respect to foods, their use has been vigorously contested by numerous food laws.

Attempts have also been made to extract the natural oxidation-inhibiting substances present in vegetable materials.

In some known processes, the oxidation-inhibiting substances are directly chemically extracted by a treatment with a basic aqueous solution.

These processes, which use a chemical agent, are also being opposed by food laws. Accordingly, it is preferred to use processes in which the oxidation-inhibiting principles are separated purely physically. These substances are normally extracted either with organic solvents or with vegetable or animal oils. The processes which use solvents involve the expensive handling of dangerous solvents which are often difficult to eliminate and which may contaminate and oxidation-inhibiting substances obtained. In addition, the solvents or oils are attended by the disadvantage that they also extract from the plant colouring substances, such as for example chlorophyll or aromatic principles, which have to be eliminated by additional deodorising and decolouring treatments. These treatments reduce the yield of oxidation-inhibiting principles and increase the cost of extraction.

Thus, one recent process described in U.S. Pat. No. 3,732,111 relates to the extraction of oxidation-inhibiting principles from spices by fine grinding in an edge mill, extraction with a vegetable oil at elevated temperature, separation by centrifuging and deodorisation by stripping with steam in vacuo at elevated temperature, the oxidation-inhibiting principles ending up in the oil.

Another process, which is described in U.S. Pat. No. 3,950,266, relates to the extraction of oxidation-inhibiting principles from spices by treating a powdered spice in a first stage with a solvent of low boiling point, filtering and drying, optionally followed by decolouration on active carbon, filtration and drying.

In a second stage, the dry extract is taken up with a vegetable oil and subjected either to stripping in a high vacuum or to molecular distillation and is then optionally purified by liquid-phase chromatography.

It has now been found that a fraction containing natural oxidation-inhibiting substances suitable for general use in foods and cosmetics and satisfying the above-mentioned requirements may be produced from vegetable materials by a treatment which does not involve any additional steps of decolouration or deodorisation or removal of solvents requiring the separation of residues and, hence, responsible for a significant reduction in the yield of oxidation-inhibiting principles.

The process according to the invention is characterised in that the previously ground vegetable material or an extract of this vegetable material obtained with a light solvent, a distillation aid and an oil are mixed, the suspension or solution is subjected to molecular distillation and a condensate containing the oxidation-inhibiting principles, the distillation aid and some of the oil used is collected.

In the context of the invention, the expression "vegetable material" is understood to include the materials which are known for their oxidation-inhibiting properties, such as spices in the form of leaves, flowers, fruits, roots, rhizomes and, in particular, plants belonging to the Labiatae family, rosemary, sage, origanum or marjoram, thyme, etc., but also vegetable residues, such as husks, pods, skins, for example cocoa skins.

One particularly advantageous starting material is formed by the residues from the extraction of the essential oils of sage and, in particular, rosemary by stripping.

These by-products of the perfume industry are ordinarily discarded or used by the perfume manufacturers as fuels in the distillation boilers.

Another interesting starting material is the powder of spices emanating from the extraction with a light solvent, for example non-denatured ethyl alcohol, of the residues from the distillation of the essential oils, followed by more or less pronounced drying of the extract.

Although it is generally preferred to use ethanol for extraction, other light solvents or mixtures of light solvents, i.e. solvents of low boiling point, may be used. Suitable solvents include methanol, dichloroethane, ethyl ether, hexane, dioxane and mixtures thereof with one another or with ethanol. In a first embodiment of the invention, the vegetable material, for example rosemary leaves which have been stripped and, preferably, ground beforehand, are extracted with a light solvent, for example ethanol. After separation of the residue, the solvent is with advantage partly evaporated under reduced pressure until the extract has a dry matter content of from 10 to 60% by weight.

In another embodiment of the invention, the vegetable material is previously ground to a particle size of from 100 to 400 microns in order to facilitate its dispersion in the oil.

The ground particles are then dispersed in an oil in a quantity of from 10 to 30% by weight of vegetable material. An oil of animal or vegetable origin may be used, although it is preferred to use a vegetable oil which has the advantage of being liquid at ambient temperature and relatively neutral from the point of view of colour and odour.

In one preferred embodiment of the process, from 0.5 to 5% by weight of water is added to the suspension intended for micronisation.

The addition of a small quantity of water before micronisation enables this water to be extremely finely dispersed in the mixture obtained. This uniformly distributed water facilitates deodorisation and decolouration during molecular distillation because, since it is eliminated with the head distillation fraction, it performs the function of entraining the colouring principles and residual odoriferous substances.

The suspension is then subjected to very fine grinding or micronisation. It has been found that very fine grinding (the particles ranging from 5 to 20 microns in size) improves the release of the oxidation-inhibiting substances present in the vegetable cells by disintegration of the cell walls.

The substances released thus end up in the oil. One very significant advantage of the very fine grinding operation is that it enables the micronised suspension to be directly treated in the molecular distillation apparatus without any need for preliminary filtration.

Any micronisation technique which enables the vegetable cells to be disintegrated may be used. It is preferred to use a ball mill which enables the vegetable cells to be intensively ground into particles ranging from 5 to 20 microns in size after one or more passages. The degree of disintegration of the vegetable particles may be determined by a suitable choice of the size of the balls and the duration and intensity of the treatment. With some vegetable materials containing more than just a few fibres, some particles ranging from a few tens to a few hundred microns in size may be left after a single micronising treatment. Rather than carrying out several successive micronising treatments, it is possible by way of modification to subject the suspension to microfiltration so that the size of the particles is the required size of 5 to 20 microns.

To prepare the mixture intended for distillation, the vegetable substance is mixed either in the form of an alcoholic extract or in the form of a micronised oily suspension with a distillation aid for the co-distillant, such as a medium-chain mono-, di- or tri-glyceride in a quantity of from 1 to 20% by weight of the mixture prepared for distillation.

It has been found that the addition of these products has several advantages:

Since they are entrained with the oxidation-inhibiting substances, the distillation aids are deposited on the condensers and promote the flow of these substances and the continuous recovery of the distillate.

In cases where a highly surface-active monoglyceride is used, it promotes the transfer of the oxidation-inhibiting principles from the light solvent to the oil and, subsequently, the thorough mixing of the distilled fraction containing the oxidation-inhibiting principles, thus facilitating their handling and metering.

They facilitate the separation of the oxidation-inhibiting substances from the oil which has served as solvent because they are entrained with these substances.

The oil is then added to the mixture of the vegetable substance and the co-distillant in such a quantity that it represents from 60 to 80% by weight of the total mixture.

In cases where the vegetable substance is in the form of an extract, for example an alcoholic extract, it has been found that the extract from which the alcohol has not been completely evaporated may with advantage be directly used in admixture with the co-distillant and the oil. The residual alcohol facilitates the decolouration and deodorisation of the fraction containing the oxidation-inhibiting principles by entraining the volatile constituents which are then condensed in the first stage of the molecular distillation apparatus.

In a variant, the alcoholic extract, the co-distillant and the oil may be mixed and the alcohol completely evaporated under reduced pressure. In another variant, the alcoholic extract and the oil may be pre-mixed, the alcohol evaporated under reduced pressure and the necessary quantities of oil and co-distillant added to the mixture obtained.

All the mixtures thus obtained are advantageously subjected to homogenisation under heat (at 60° to 70° C. where the mixture contains alcohol or at 90° to 130° C. where the alcohol has been previously evaporated).

When the starting material is a rosemary extract obtained by extraction with an alcohol or a residue from the distillation of the essential oils of rosemary, it has been found to be of advantage to subject the solution or the micronised suspension to a heat treatment. This is because a fraction representing approximately 5% of the dry extract has been observed to undergo carbonisation under the high temperature conditions prevailing during distillation.

During the molecular distillation step, this fraction tends to be deposited on the condensers and contaminates the condensate. The solution or suspension is heated for 1 to 5 minutes to approximately 200°–250° C., for example in a scraped-surface exchanger, and the carbonised fraction is separated, for example by sieving or centrifuging. The solution or suspension is then ready for distillation.

In a variant, the suspension may be subjected to a heat treatment which does not go as far as carbonisation, for example over a period of from 5 to 10 minutes at a temperature in the range from 100° to 200° C. In this case, the sieving or centrifuging operation is optional.

The molecular distillation of the solution or suspension containing the added distillation aid and optionally freed from the fraction capable of carbonising may be carried out in any suitable apparatus, such as a falling-film evaporator or a centrifugal rotating-disc evaporator. The liquid is kept in a dwell tank at 60° to 90° C. and then introduced into the apparatus. The apparatus comprises a first stage of which the evaporation surface is kept at 110° to 180° C., the condensation surface being at 80° to 160° C., and in which a vacuum of from 0.005 to 0.2 Torr prevails. The vacuum may be generated by a vane pump coupled with traps, for example of liquid nitrogen, kept at −196° C. In this first stage, the mixture is simultaneously degassed, decoloured and deodorised. As mentioned above, the water which has been added to the mixture serves to entrain the residual colouring and odoriferous principles and is separated as first condensate.

In a second stage, in which a vacuum of less than 0.005 Torr prevails, the fraction containing the oxidation-inhibiting compounds is separated in the form of condensate, the evaporation surface being kept at 190° to 280° C. whereas the condensation surface is at 80° to 160° C. The distillate consists essentially of the oil which has served as solvent. It may be recycled to the head of the line and re-used for the preparation of the mixture to be distilled, for micronisation or for standardisation of the micronised mixture.

The throughput of product subjected to the molecular distillation step may vary from 0.5 to 7 kg/hour, depending on the working conditions.

It has been found that the extraction yield, based on the oxidation-inhibiting principles, is much higher in the process according to the invention than in analogous processes because the solutions or suspensions subjected to the molecular distillation step contain from 5 to 20% by weight of the vegetable starting material as against 1 to 2% by weight, for example for the solutions treated in accordance with U.S. Pat. No. 3,950,266. In the preferred variant of treating an alcoholic extract with preliminary partial evaporation of the alcohol, molecular distillation is carried out in a single stage, enabling the fraction rich in oxidation-inhibiting principles to be isolated whilst, at the same time, effecting its discolouration, deodorisation and separation from the oil.

In addition, the association of micronisation in the oil with molecular distillation of the suspension enables the oxidation-inhibiting principles of vegetable materials to be isolated without preliminary extraction, for example in the case of more or less dried cocoa skins. Irrespective of the starting material used and its preliminary treatment (micronisation or extraction), the fraction obtained contains oxidation-inhibiting principles equal or superior in their oxidation-inhibiting effect to synthetic oxidation inhibitors. On the other hand, the harmlessness of this fraction and its relative organoleptic neutrality are remarkable. The process according to the invention enables the oxidation-inhibiting principles to be stored in concentrated solution (for example 40% by weight) for a prolonged period (at least 1 year at ambient temperature) without any reduction in their oxidation-inhibiting effect or organoleptic alteration, which is definitely not the case with the conventional chemical oxidation inhibitors of the B.H.A or B.H.T type.

Finally, it has been found that if the condensate obtained in accordance with the invention is ground with from 5 to 40%, based on the weight of the condensate, of citric or ascorbic acid or their salts and esters, for example in mills equipped with granite cylinders, a synergy is observed which increases the oxidation-inhibiting effect by between 7 and 12 times, as measured by ASTELL's induction time method.

The oxidation-inhibiting substances obtained may be used for stabilising all kinds of food or cosmetic products against oxidation. They may be incorporated in the products by any known means, for example in solution, suspension or emulsion in solvents, liquefied gases or the like, i.e. by means of a vehicle.

Foods in which the oxidation-inhibiting substances may be incorporated include fats, such as vegetable oils or animal fats, emulsions of the mayonnaise type, spreading paste, stock cubes, moist products containing bound fats, such as meat, fish or dried, for example freeze-dried, products, cereals, malted milk, reconstituted whole milk powder, dry vegetables and, in particular, potato flakes.

The cosmetic products sensitive to oxidation in which the oxidation-inhibiting principles obtained in accordance with the invention are advantageously incorporated are in the form of aqueous dispersions (lotions, such as pre-shave or after-shave lotions), fluid emulsions (body milks, cleansing milks), creams (white cream, sun cream), pastes (masks), etc. Their protection against oxidation makes it possible in particular to avoid the olfactory problems due to rancidity.

Satisfactory results are obtained by incorporating from 0.05 to 1% of the condensate, i.e. from 0.01 to 0.2% of entrainable active substance, part of the condensate being formed by the entrained oil and the distillation vehicle.

The process according to the invention is illustrated by the following non-limiting examples in which the percentages and quantities quoted are by weight unless otherwise indicated.

EXAMPLE 1

Stripped needles of rosemary emanating from the extraction of the essential oils are subjected to dry grinding in an ALPINE mill (interval between discs 0.8 mm, rotor speed 900 r.p.m.) until particles ranging from 100 to 400 microns in size are obtained. 17 parts of ground rosemary are mixed with 83 parts of peanut oil and from 0.5 to 5% of water is added to the mixture. The suspension is treated in a DINO ball mill comprising agitator discs with a separator spaced at 0.2 mm (circumferential speed of the discs 10 m/second), four fifths of the grinding chamber being filled with balls from 1 to 1.5 mm in diameter. Micronisation is carried out in two passes with a residence time of 3.5 minutes. A suspension having a viscosity of 210 centipoises measured at 25° C. is thus obtained.

The micronised suspension is subjected to a heat treatment by passage for 1 minute through a scraped-surface heat exchanger at 200° C., and is then introduced into a 0.15 mm mesh sieve in order to separate the carbonised fraction corresponding to approximately 5% of the dry extract.

The suspension is standardised by the addition of an equal quantity of peanut oil and a monoglyceride (for example DIMODAN S, a product of the Grinsted company) is added in a quantity of 7 parts for 93 parts of the standardised micronised suspension which is then transferred to a dwell tank tempered to 70° C.

The molecular distillation of the suspension is carried out in a LEYBOLD two-stage falling-film evaporator having an active surface of the heat exchanger of 0.1 m² and a rotational speed of from 25 to 600 r.p.m. under the following conditions:

| throughput | 0.5 to 1 kg/hour |
|---|---|
| temperature of the traps | −196° C. |
| temperature of the heated surface in the first stage | 120° C.–160° C. |
| temperature of the condenser in the first stage | 90° C.–150° C. |
| vacuum in the first stage | 0.005 mm Hg |
| temperature of the heated surface in the second stage | 200° C.–230° C. |
| temperature of the condenser in the second stage | 90° C.–150° C. |
| vacuum in the second stage | 0.001 mm Hg |

The amber-coloured condensate of the second stage is collected. It has a very feint taste and odour and represents from 8 to 12% (calculated without the co-distillant) of the treated rosemary leaves.

EXAMPLE 2

Stripped needles of rosemary emanating from the distillation of essential oil are extracted under reflux with non-denatured ethyl alcohol and the extract dried or partially dried.

15 parts of the extract are mixed with 85 parts of peanut oil and from 1 to 5% of water are added to the mixture.

Micronisation is carried out in the same way as in Example 1, but without preliminary grinding, until a suspension having a viscosity of 435 centipoises (as measured at 25° C.) and a particle size of approximately 5 microns is obtained.

The micronised suspension is subjected to a heat treatment by passage for 1 minute through a scraped-surface heat exchanger at 200° C. and is then passed through a 0.15 mm mesh sieve to separate the carbonised fraction corresponding to approximately 5% of the dry extract.

The sieved oily suspension is standardised by the addition of peanut oil in a quantity of from 3 to 4 parts per part of suspension and a medium-chain triglyceride is added in a quantity of 5 parts for 95 parts of the standardised suspension. The standardised suspension is then transferred to a dwell tank tempered to 70° C. The mixture is then subjected to molecular distillation under the same working conditions as in Example 1. The amber-coloured condensate of the second stage is collected, being characterised by a very feint taste and odour and representing 85% of the treated alcoholic extract.

EXAMPLE 3

The procedure is as in Example 2, except that the carbonisation step is replaced by a heat treatment of the suspension for 5 to 10 minutes at 130° C., followed by centrifuging at 85° C. The condensate of the second stage is collected. It is light amber in colour, has a very feint odour and taste and represents 60% of the treated alcoholic extract.

EXAMPLES 4 to 6

Stripped needles of rosemary emanating from the distillation of essential oil are extracted with non-denatured ethyl alcohol. The extract is freed from the residues by filtration or centrifuging and the alcohol evaporated under reduced pressure to a dry matter content of from 45 to 50%. 10 parts of extract are mixed with 10 parts of co-distillant (monoglyceride, for example DIMODAN S, a product of the Grinsted company) and 80 parts of peanut oil. The mixture is homogenised at 60° to 70° C. and treated as shown in Table I below:

TABLE I

| Example No. | Heat treatment for 2 minutes at 200° C.-250° C. | Filtration or centrifuging | Yield calculated without co-distillant in % of the treated rosemary leaves |
|---|---|---|---|
| 4 | − | − | 16–17 |
| 5 | + | − | 15–16 |
| 6 | + | + | 15–16 |

The mixture is then subjected to molecular distillation in the same way as in Example 1. The condensate of the second stage is collected. It has a feint odour and taste, contains the oxidation-inhibiting principles and represents the yield in relation to the treated alcoholic extract indicated in Table I, whilst the distillate essentially formed by the peanut oil is recycled to be used again.

EXAMPLES 7 to 9

30 parts of the alcoholic rosemary extract obtained in the same way as in Examples 4 to 6 are mixed with 70 parts of peanut oil and the evaporation of the alcohol is completed under reduced pressure. 27 parts of the mixture obtained are then mixed with 63 parts of peanut oil and 10 parts of co-distillant (monoglyceride for example DIMODAN S, a product of the Grinsted company), after which the whole is homogenised for 2 minutes at 90° to 130° C. The mixture is then treated as indicated in Table II below:

TABLE II

| Example No. | Heat treatment for 2 minutes at 200° C.-250° C. | Filtration or centrifuging at 100° C. | Yield calculated without co-distillant in % of the treated rosemary leaves |
|---|---|---|---|
| 7 | − | − | 14 |
| 8 | + | − | 13 |
| 9 | + | + | 13 |

The subsequent operations are the same as in Examples 4 to 6 and the results obtained comparable.

EXAMPLES 10 to 12

10 parts of the alcoholic rosemary extract obtained as in Examples 4 to 6 are mixed with 80 parts of peanut oil and 10 parts of co-distillant (monoglyceride, for example DIMODAN S, a product of the Grinsted company) and the alcohol is evaporated under reduced pressure.

The whole is homogenised for 2 minutes at 90° to 130° C. and then treated as indicated in Table III below:

TABLE III

| Example No. | Heat treatment for 2 minutes at 200° C.-250° C. | Filtration or centrifuging 100° C. | Yield calculated without co-distillant in % of the treated rosemary leaves |
|---|---|---|---|
| 10 | − | − | 14 |
| 11 | + | − | 13 |
| 12 | + | + | 13 |

The subsequent operations are the same as in Examples 4 to 6 and the results obtained comparable.

EXAMPLE 13

The oxygen absorption of various condensates obtained by micronisation or extraction and molecular distillation under the conditions of Examples 1, 2 and 6 is measured by ASTELL's method. This method comprises measuring the oxygen absorption of fats and oils as a function of time under precise temperature conditions and recording the induction period in relation to a reference sample. It is described in "BFMIRA Tech. Cricular No. 487, July 1971, Meora M. L., Rosie D. A., A Sensitive oxygen absorption apparatus for studying the stability of fats."

The substrate is 4 g of chicken fat containing 1000 ppm of extract based on the quantity of entrainable oxidation-inhibiting substance contained in the vegetable material, the atmosphere above the sample being air whilst the temperature is 90° C. The results obtained are set out in Table IV below:

TABLE IV

| Type of extract | Induction time (hours) |
|---|---|
| Chicken fat without any oxidation-inhibiting substance | 3–4 |
| Chicken fat + 1000 ppm of entrainable active substance from rosemary according to Example 1 | 18–20 |
| Chicken fat + 1000 ppm of entrainable active substance from rosemary according to Example 2 | 20–25 |
| Chicken fat + 1000 ppm of entrainable active substance from rosemary according to Example 6 | 20–25 |
| Chicken fat + 1000 ppm of entrainable active substance from sage obtained in accordance Example 1 | 25–30 |
| Chicken fat + 1000 ppm of entrainable active substance from cocoa skins obtained in accordance |  |

TABLE IV-continued

| Type of extract | Induction time (hours) |
| --- | --- |
| with Example 1 | 18-20 |
| Chicken fat + 1000 ppm of a mixture of equal parts by weight of butyl hydroxy anisole (BHA) and butyl hydroxy toluene (BHT) | 20-25 |

EXAMPLE 14

A quantity corresponding to 300 ppm of entrainable active substance from rosemary obtained as described in Examples 1 to 13 is added to potato flakes during the preparation of instant mashed potato.

The degradation of the lipids contained in this product is followed by measuring the formation of pentane in the head space which emanates from the degradation of the octadecadienoic acid present, the pentane being determined by gas-phase chromatography using the method described by M. Arnaud and J. J. Wuhrmann, in "Dehydrated food oxidation as measured by thermal release of hydrocarbons," 4th International Congress of Food Science and Technology, Madrid 23-27.9.1974.

The effectiveness of the oxidation-inhibiting power of the condensates is shown in Table V below:

TABLE V

| | Potato flakes | |
| --- | --- | --- |
| Storage in months at 30° C. | With no addition | $UI \times 10^3$ of pentane with addition of 300 ppm of entrainable active substance |
| 0 | 0 | 0 |
| 1 | 8 | 0.2 |
| 3 | 17 | 4 |
| 3 | 26 | 8.5 |

EXAMPLE 15

A quantity of condensate of rosemary obtained as described in Examples 1 to 13 corresponding to 500 ppm of entrainable active substance is added to a prebaked cornflour before final drying. The degradation of the lipids in the product is followed in the same way as in the preceding Example and the effectiveness of the oxidation inhibitor is determined with the results shown in Table VI below:

TABLE VI

| | Prebaked cornflour | |
| --- | --- | --- |
| Storage in months at 30° C. | With no addition | $UI \cdot 10^5$ of pentane with addition of 500 ppm |
| 0 | 0 | 0 |
| 1 | 3.6 | 1.8 |
| 2 | 8.9 | 2.1 |
| 3 | 13.6 | 4.7 |

EXAMPLE 16

The condensate obtained in accordance with Example 6 is ground with 10% of ascorbic acid (based on the weight of the condensate) in a mill equipped with granite rollers.

The oxidation-inhibiting effect of the ground mixture is measured by ASTELL's method as in Example 13.

For 0.2% of mixture, the induction time is found to be between 140 and 160 hours, which corresponds to a 7 to 9 fold increase in the oxidation inhibiting effect of the condensate on its own.

If mixing is carried out in the same proportions without grinding, the induction time obtained is 75 hours. Accordingly, there is a synergic effect.

EXAMPLE 17

A white cream of the oil-in-water emulsion type is prepared by mixing the following ingredients:

| | | |
| --- | --- | --- |
| 1. | Polyoxyethylene stearyl ether | 2% |
| | Polyoxyethylene cetyl ether | 2% |
| | Self-emulsifiable glycerol monostearate | 4% |
| | Cosbiol (perhydrasqualene) | 5% |
| | Soya oil | 5% |
| | Mineral oil | 15% |
| | Stearic acid | 2% |
| | Condensate of Example 6 | 0.2% |
| 2. | Triethanolamine | 0.4% |
| 3. | Carbopol ® 941 (a Goodrich product) | 0.4% |
| | Methyl p-oxybenzoate | 0.3% |
| | Sterile demineralised water | balance to 100% |
| 4. | Perfume | as required |

The procedure comprises heating the fat phase (1), to which the oxidation-inhibiting condensate has been previously added, to between 80° and 85° C. and subsequently heating the sterile demineralised water of phase (3) to the same temperature. The preservative is dissolved in the sterile demineralised water, after which (the temperature being 70° C.) the Carbopol is introduced and the mixture is left to swell for a few hours. The emulsion is prepared at 80° to 85° C. by pouring phase (1) into phase (3) to which phase (2), i.e. the triethanolamine, has been previously added. The emulsion is completed by stirring with a turbine for 15 minutes. It is then cooled to 35° C. for the addition of phase (4). At 25° C., the cream is complete.

This cream has a pleasant protective effect coupled with high stability.

EXAMPLE 18

A white cream of the water-in-oil emulsion type is prepared by mixing the following ingredients:

| | |
| --- | --- |
| Magnesium lanolate | 0.9% |
| Lanoline alcohol | 8.1% |
| Paraffin oil | 38.7% |
| Avocado oil | 0.3% |
| Ozocerite | 2.0% |
| Methyl p-oxybenzoate | 0.3% |
| Condensate of Example 6 | 0.2% |
| Sterile demineralised water | balance to 100% |
| Perfume | as required |

To this end, the magnesium lanolate is dissolved in the paraffin oil at approximately 100° C., after which the solution obtained is cooled to 80° C. before introduction of the lanoline alcohol and the ozocerite. After cooling to 40° C., the avocado oil and the oxidation-inhibiting condensate are introduced, followed by the addition with vigorous stirring of the aqueous medium containing the preservative. The mixture is then cooled with slow stirring to ambient temperature and the preparation is completed by addition of the perfume.

The cream obtained shows excellent stability in storage.

We claim:

1. A process for the production of a fraction containing oxidation-inhibiting substances from a vegetable material rich in these substances comprising:
   (a) mixing a ground vegetable material or an extract of this vegetable material obtained with a solvent selected from the group consisting of methanol, dichloroethane, ethyl ether, hexane, dioxane, ethanol and mixtures thereof; a co-distillant which is a mono-, di- or triglyceride of a $C_{8-10}$ fatty acid; and a vegetable oil to form a suspension or solution, wherein the amount of co-distillant present in the suspension or solution is in the amount of from 1 to 20% by weight of the total weight;
   (b) heating the suspension or solution for 1 to 15 minutes to 100° to 250° C. and separating a carbonised solid fraction by sieving or centrifuging;
   (c) subjecting the suspension or solution to molecular distillation; and
   (d) collecting a condensate containing the oxidation-inhibiting principles, the co-distillant and a portion of the vegetable oil used.

2. The process of claim 1, wherein the vegetable material treated is residue obtained after the extraction of essential oil of rosemary.

3. The process of claim 1, wherein the solution to be distilled is prepared by extracting the vegetable material with the solvent, evaporating the solvent under reduced pressure before or after the addition of a vegetable oil and a co-distillant and then homogenising the resulting mixture.

4. The process of claim 1, wherein the molecular distillation step is carried out under a vacuum of less than 0.005 Torr. at a temperature of from 190° to 280° C. and with a throughput of material of from 0.5 to 7 kg per hour.

5. A process for the production of a fraction containing oxidation-inhibiting substances from a vegetable rich in these substances comprising:
   (a) suspending a ground vegetable material in a vegetable oil such that the amount of oil present is from 70% to 90% by weight of the total weight;
   (b) micronising the oily suspension to obtain particles of at most 20 microns in size;
   (c) adding further vegetable oil and a co-distillant which is a mono-, di- or triglyceride or a $C_{8-10}$ fatty acid such that the amount of vegetable oil present in the resulting suspension is from 60% to 80% by weight of the total weight and the amount of co-distillant present in from 1 to 20% by weight of the total weight;
   (d) homogenising the suspension;
   (e) subjecting the suspension to molecular distillation; and then
   (f) collecting a condensate containing the oxidation-inhibiting principles, the co-distillant and a portion of the vegetable oil used.

6. The process of claim 5, wherein the vegetable material treated is rosemary, sage or cocoa skins.

7. The process of claim 5, wherein micronisation is carried out by passing a suspension containing from 10 to 30% by weight of the vegetable material one or more times through a ball mill.

8. The process of claim 7, wherein from 0.5 to 5% by weight of water is added to the suspension before micronisation.

* * * * *